(12) United States Patent
Nutalapati

(10) Patent No.: US 10,485,798 B2
(45) Date of Patent: Nov. 26, 2019

(54) METHYLNALTREXONE NASAL FORMULATIONS, METHODS OF MAKING, AND USE THEREOF

(71) Applicant: Siva Rama K. Nutalapati, Princeton, NJ (US)

(72) Inventor: Siva Rama K. Nutalapati, Princeton, NJ (US)

(73) Assignee: APTAPHARMA INC., Pennsauken, NJ (US)

(*) Notice: Subject to any disclaimer, the term of this patent is extended or adjusted under 35 U.S.C. 154(b) by 375 days.

(21) Appl. No.: 13/971,870

(22) Filed: Aug. 21, 2013

(65) Prior Publication Data

US 2014/0057934 A1 Feb. 27, 2014

Related U.S. Application Data

(60) Provisional application No. 61/691,943, filed on Aug. 22, 2012.

(51) Int. Cl.
*A61K 31/485* (2006.01)
*A61P 1/10* (2006.01)
*A61M 11/02* (2006.01)
*A61M 15/08* (2006.01)

(52) U.S. Cl.
CPC ............ *A61K 31/485* (2013.01); *A61M 11/02* (2013.01); *A61M 15/08* (2013.01)

(58) Field of Classification Search
CPC .................................................... A61K 31/485
USPC .............................. 514/282; 546/45; 424/434
See application file for complete search history.

(56) References Cited

U.S. PATENT DOCUMENTS

| | | | |
|---|---|---|---|
| 7,696,220 B2 | 4/2010 | Farrar et al. | |
| 2003/0022909 A1 | 1/2003 | Moss et al. | |
| 2004/0180916 A1 | 9/2004 | Levine | |
| 2005/0004155 A1 | 1/2005 | Boyd et al. | |
| 2005/0245483 A1 | 11/2005 | Brogmann et al. | |
| 2008/0194611 A1 | 8/2008 | Alverdy et al. | |
| 2009/0246256 A1 | 10/2009 | Al-Ghananeem | |
| 2010/0267758 A1 | 10/2010 | Sanghvi et al. | |
| 2010/0305323 A1 | 12/2010 | Smolenskaya et al. | |
| 2010/0311781 A1 | 12/2010 | Doshan et al. | |
| 2011/0250278 A1* | 10/2011 | Yuan | 424/490 |
| 2012/0136019 A1 | 5/2012 | Boyd et al. | |

FOREIGN PATENT DOCUMENTS

WO 2007053194 A2 5/2007
WO 2010002576 A1 1/2010

OTHER PUBLICATIONS

Ugwoke et al. Advanced Drug Delivery Reviews 2005, 57, 1640-1665.*
Ilium et al. Journal of Pharmacology and Experimental Therapeutics JPET 2002, 301, 391-400.*
Fernandez-Urrusuno et al. Pharmaceutical Research 1999, 16 (1), 1576-1581.*

* cited by examiner

*Primary Examiner* — Irina Neagu
(74) *Attorney, Agent, or Firm* — Cantor Colburn LLP

(57) ABSTRACT

Methylnaltrexone nasal formulations are discloses which provide improved bioavailability over oral dosage forms and improved patient compliance over injectable dosage forms. Also disclosed are methods of making the nasal formulations and methods of using, specifically to treat the side effects of opioid drug use, such as constipation, and other indications.

24 Claims, No Drawings

METHYLNALTREXONE NASAL FORMULATIONS, METHODS OF MAKING, AND USE THEREOF

CROSS-REFERENCE TO RELATED APPLICATIONS

This application claims the benefit of U.S. Provisional Application Ser. No. 61/691,943 filed Aug. 22, 2012, which is incorporated herein by reference in its entirety.

BACKGROUND

Clinicians often use opioids to treat patients with moderate-to-severe pain. Opioids, however, often result in side effects such as inducing or aggravating constipation as these drugs react at receptors outside the targeted central nervous system. Severe opioid-induced constipation may result in patient refusal to be treated with opioid therapy.

Opioid-induced constipation is predominantly mediated by gastrointestinal μ-opioid receptors as well as kappa receptors. Selective blockade of these peripheral receptors might relieve constipation without compromising centrally mediated effects of opioid analgesia or precipitating withdrawal.

Methylnaltrexone is a quaternary derivative of naltrexone and a peripherally-acting μ-opioid antagonist. It has restricted ability to cross the blood-brain barrier in humans because of its polarity and low lipid solubility. In healthy volunteers, intravenous or oral administration of methylnaltrexone was found to reverse opioid-induced reduction in bowel motility without affecting analgesia.

Methylnaltrexone and methylnaltrexone salts have poor absorption in the gastrointestinal system thereby rending orally administered methylnaltrexone with limited bioavailability.

Methylnaltrexone bromide is currently available as a subcutaneous injection to treat the side effects of opioid drug use, such as opioid-induced constipation. The dosage amount for the subcutaneous route is approximately 0.15 mg/kg while the oral route is approximately 3.2 mg/kg to 6.4 mg/kg, which is about twenty times higher than the subcutaneous route.

Thus, there remains a need in the art for formulations and methods of administering methylnaltrexone that will require lower doses compared to orally administered formulations and better patient compliance compared to subcutaneous and injectable formulations.

SUMMARY

In one embodiment, a liquid mucoadhesive intranasal dosage formulation comprises methylnaltrexone, a pharmaceutically acceptable salt of methylnaltrexone, a pharmaceutically acceptable ester of methylnaltrexone, or a combination thereof; a mucoadhesive agent; and a liquid carrier; wherein the formulation does not substantially drip from the intranasal cavity after administration of a single dose In one embodiment, a method of administering methylnaltrexone to a patient in need thereof comprises intranasally administering to a patient a liquid mucoadhesive intranasal dosage formulation comprising methylnaltrexone, a pharmaceutically acceptable salt of methylnaltrexone, a pharmaceutically acceptable ester of methylnaltrexone, or a combination thereof; a mucoadhesive; and a liquid carrier, wherein the formulation does not substantially drip from the intranasal cavity after administration of a single dose.

DETAILED DESCRIPTION

Disclosed herein are viscous or shear thinning liquid mucoadhesive intranasal dosage formulations of methylnaltrexone, a pharmaceutically acceptable salt of methylnaltrexone, a pharmaceutically acceptable ester of methylnaltrexone, or a combination thereof which do not substantially drip or which do not drip out of the patient's nasal cavity after a single dose has been administered. There are many advantages to these formulations including ease of administration for example by spraying, improved bioavailability compared to oral methylnaltrexone formulations, and smaller doses compared to oral formulations resulting in fewer side effects. Additionally, the nasal formulations will have better patient compliance compared to injectable formulations.

Administration of methylnaltrexone to the nasal mucosa allows for faster onset and higher bioavailability compared to oral administration.

Administration of methylnaltrexone intranasally requires less active agent compared to oral formulations, and thus there is reduced toxicity.

Since intranasally administered methylnaltrexone is not absorbed through the gut, the first pass effect is avoided to result in higher bioavailability.

In an embodiment, a small volume (e.g. <200 microliters) of mucoadhesive nasal formulation will adhere to the nasal mucosa and will not cause any post nasal drip into the throat.

The liquid nasal formulation is formulated in a way that allows for the adherence to the nasal cavity of the patient without substantial loss of formulation to the back of the patient's throat. Preparation of a formulation with a mucoadhesive agent and having an adequate viscosity results in a formulation that does not leak down the back of the nasal cavity into the patient's throat and eventually to the gastrointestinal tract where the active agent is less bioavailable. Furthermore, to avoid loss of the formulation out of the nasal cavity and to promote absorption of the active, the formulation is administered in small amounts (e.g. about 50 to about 200 microliters per dose). Additionally, a nasal inhaler/spray system can be used to avoid post-nasal runoff, aftertaste, or drip. Since, the bioavailability of methylnaltrexone is less through oral route compared to the nasal route, any drug that drips into the throat will enter the gastrointestinal tract resulting in decreased bioavailability and/or high variations in bioavailability. Thus, the nasal formulations comprise a mucoadhesive agent to increase the viscosity of the formulations and to provide longer residence times on the nasal mucosa partially due to physical forces that resist nasal cilia clearance. The resulting formulation does not drip or does not substantially drip from the patient's intranasal cavity after a single dose of the formulation has been administered.

Disclosed herein are liquid mucoadhesive intranasal dosage formulations comprising methylnaltrexone, a pharmaceutically acceptable salt of methylnaltrexone, a pharmaceutically acceptable ester of methylnaltrexone, or a combination thereof a mucoadhesive agent; and a liquid carrier, wherein the mucoadhesive is viscous and thixotropic in nature, and wherein the formulation does not substantially drip or does not drip from the intranasal cavity after administration.

As used herein, "nasal administration" means the same as "intranasal administration" wherein the formulation is administered to the interior of the nasal cavity.

As used herein, "does not substantially drip from the intranasal cavity after administration" means there is less than 10% of the intranasally administered dose of formulation that migrates out of the external nares or from the nasopharynx to the laryngopharynx and pharynx.

The formulation comprises methylnaltrexone, a pharmaceutically acceptable salt of methylnaltrexone, a pharmaceutically acceptable ester of methylnaltrexone, or a combination thereof. An exemplary methylnaltrexone salt is methylnaltrexone bromide.

"Pharmaceutically acceptable salt" includes derivatives of a compound, wherein the compound is modified by making acid or base addition salts thereof, and with regard to an active agent further refers to pharmaceutically acceptable solvates, including hydrates, crystalline forms, non-crystalline forms, and polymorphs, of such salts. Examples of pharmaceutically acceptable salts include, but are not limited to, mineral or organic acid addition salts of basic residues such as amines; alkali or organic addition salts of acidic residues; and the like, or a combination thereof. For example, acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, or a combination thereof. Pharmaceutically acceptable organic salts includes salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparginate, glutamate, and the like; or a combination thereof.

The methylnaltrexone, a pharmaceutically acceptable salt of methylnaltrexone, a pharmaceutically acceptable ester of methylnaltrexone, or a combination thereof can be present in the liquid mucoadhesive intranasal dosage formulation in an amount about 4 to about 200 mg of methylnaltrexone per dose, specifically about 5 to about 150 mg per dose, and yet more specifically 8 to about 100 mg per dose.

The liquid mucoadhesive intranasal dosage formulation further comprises a mucoadhesive agent. The mucoadhesive agent imparts a mucoadhesive property to the formulation so that the formulation remains in the nasal cavity and does not drip out of the nose either from the external nares (nostrils) or the back of the throat. Nasal Mucociliary Clearance is one of the limiting factors for nasal drug delivery, because it reduces the time allowed for drug absorption. Thus, improving nasal drug absorption can be achieved by prolonging the contact time between the drug and the nasal mucosa. Mucoadhesion implies the attachment of the drug formulation to the nasal mucus membranes, involving an interaction between mucin and a mucoadhesive agent, a synthetic or natural polymer. The sequential events that occur during mucoadhesion include a first step where the mucoadhesive agent absorbs water from the nasal mucosa and swells. The mucoadhesive agent then intimately penetrates into the nasal mucosa and, hence, localizes the formulation in nasal cavity, enhancing the drug concentration gradient across the epithelium.

Exemplary mucoadhesive agents include an alginate (e.g. sodium alginate), a cellulose and cellulose derivatives (e.g. carboxymethylcellulose, hydroxypropyl cellulose, hydroxyethyl cellulose, microcrystalline cellulose, a combination thereof, and the like), chitosan, gelling proteins (e.g. gelatin), hydroxyethyl methacrylate, a modified starch (e.g. thermally modified starch, and the like), natural gums and polysaccharides (e.g. Acacia, gum Arabic, Guar gum, gum Karaya, pectin, tragacanth, a combination thereof, and the like), a polyacrylic acid (e.g. CARBOPOL® 934P from Lubrizol CAS no. 9003-01-4), a poly(acrylic acid/divinyl benzene), a poly(lactic acid), a polycarbophil (i.e. polyacrylic acid cross-linked with divinyl glycol), polyvinyl pyrrolidone, psyllium, a resin (e.g. Amberlite-200 a cation exchange resin based on sulfonic acid exchange groups on a polystyrenic matrix, and the like), or a combination thereof. Specific mucoadhesive agents include microcrystalline cellulose, carboxymethylcellulose sodium, polyvinyl pyrrolidone, or a combination thereof.

The mucoadhesive agent can be present in the formulation in an amount of about 1.0 to about 25% w/v, specifically about 2.0 to about 10, and more specifically about 3.0 to about 5% w/v.

The formulation further comprises a pharmaceutically acceptable liquid carrier to dissolve or suspend the ingredients. Exemplary pharmaceutically acceptable liquid carriers include purified water; and pharmaceutically acceptable organic liquid carriers, for example glycerin; propylene glycol; a lower molecular weight polyethylene glycol (e.g., polyethylene glycol 200, polyethylene glycol 300, polyethylene glycol 400, polyethylene glycol 540, polyethylene glycol 600, and the like); ethanol; propylene carbonate; or a combination thereof.

The formulation can optionally further comprise an intranasal formulation excipient such as a buffering agent, a flavoring agent, a sweetening agent, a tonicity agent, an antimicrobial preservative, an antimicrobial preservative synergist, a surfactant, an emulsifier, a solubilizer, an absorption enhancer, or a combination thereof. In some instances, a single compound or material will meet two or more of the foregoing general classifications. For example, a compound may function as both an emulsifier and a surfactant.

The liquid mucoadhesive intranasal dosage formulation can further include an antimicrobial preservative to prevent the unwanted growth of bacteria, molds, fungi, or yeast. Examples of suitable antimicrobial preservatives include benzyl alcohol, benzalkonium chloride, benzoic acid alkali metal salts (e.g., sodium benzoate), sorbic acid alkali metal salts (e.g., potassium sorbate), sodium erythorbate, sodium nitrite, calcium sorbate, butylated hydroxyanisole (BHA), butylated hydroxytoluene (BHT), parabens (e.g., lower alkyl esters of para-hydroxybenzoic acid), alkali metal salts of parabens including sodium and potassium salts of methyl-, ethyl-, propyl-, or butylparaben, or a combination thereof. Specific antimicrobial preservatives include benzyl alcohol, benzalkonium chloride, or a combination thereof.

The antimicrobial preservative can be present in the liquid mucoadhesive intranasal dosage formulation in an amount of about 0.001 to about 1.0% w/v, specifically about 0.01 to about 0.55% w/v, and yet more specifically about 0.1 to about 0.3% w/v.

The liquid mucoadhesive intranasal dosage formulation can further optionally include an antimicrobial preservative synergist such as ethylenediaminetetraacetic acid (EDTA) or pharmaceutically acceptable salts there of (e.g. calcium disodium EDTA). The antimicrobial preservative synergist can be present in the formulation in an amount of about 0.001 to about 0.1% w/v, specifically about 0.01 to about 0.05% w/v, and more specifically about 0.02 to about 0.04% w/v.

The liquid mucoadhesive intranasal dosage formulation can be isotonic or isotonic and buffered. The liquid mucoadhesive intranasal dosage formulation may optionally comprise a tonicity agent such as dextrose, glycerin, mannitol, potassium chloride, sodium chloride, or a combination thereof. The amount of tonicity agent can be determined by one having ordinary skill in the art without undue experimentation.

The liquid mucoadhesive intranasal dosage formulation can comprise a buffering agent. Exemplary buffering agents include citrates, acetates, phosphates (e.g. citric acid, sodium citrate, sodium acetate, dibasic sodium phosphate, monobasic sodium phosphate, or a combination thereof).

In an embodiment, the liquid carrier comprising non-active ingredients for use to prepare the mucoadhesive intranasal dosage formulation can have a pH of about 5.5 to about 7.5, specifically about 6.0 to about 7.0.

A sweetening agent can optionally be included in the formulation to make the composition palatable to the patient and to improve patient compliance. Exemplary sweetening agents include sugar alcohols (or polyols), such as glycerol, sorbitol, xylitol, mannitol, galactitol, maltitol, hydrogenated isomaltulose (isomalt), lactitol, erythritol, glucitol, ribitol, or a combination thereof; sugar sweeteners generally include saccharides, such as mono-saccharides, di-saccharides and poly-saccharides such as sucrose (saccharose, sugar), dextrose, maltose, dextrin, maltodextrin, xylose, ribose, glucose (including liquid glucose), mannose, galactose, fructose (levulose), lactose, invert sugar, fructo oligo saccharide syrups, trehalose, tagatose, fucose, gulose, raffinose, ribulose, rufinose, stachyose, xylulose, adonose, amylase, arabinose, deoxyribose, corn syrup solids, such as high fructose corn syrup, or a combination thereof; artificial sweeteners such as soluble saccharin salts, i.e., sodium or calcium saccharin salts, the potassium salt of 3,4-dihydro-6-methyl-1,2,3-oxathiazine-4-one-2,2-dioxide (Acesulfame-K), the free acid form of saccharin, L-aspartic acid derived sweeteners, such as L-aspartyl-L-phenylalanine methyl ester (Aspartame), L-alphaaspartyl-N-(2,2,4,4-tetramethyl-3-thietanyl)-D-alaninamide hydrate (Alitame), N—[N-(3,3-dimethylbutyl)-L-aspartyl]-L-phenylalanine 1-methyl ester (Neotame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, or a combination thereof; sucralose; maltol; or a combination thereof.

When used, the sweetening agent can be present in the liquid mucoadhesive intranasal dosage formulation in an amount of about 0.1 to about 10% w/v, specifically about 0.2 to about 5.0% w/v, and more specifically about 0.5 to about 3.0% w/v. The amount of sweetening agent can be determined by one of ordinary skill in the art without undue experimentation.

The liquid mucoadhesive intranasal dosage formulation may optionally further comprise a flavoring agent. Flavoring agents include those flavors known to one of ordinary skill in the art, such as natural flavors and artificial flavors. Suitable amounts of flavoring agent can be selected by one of ordinary skill in the art without undue experimentation. In one embodiment, the flavoring agent can be present in the liquid composition from about 0.1 to about 5.0% w/v, specifically about 0.15 to about 3% w/v, and more specifically about 1.0 to about 2.0% w/v.

The liquid mucoadhesive intranasal dosage formulations may further comprise a surfactant (ionic, non-ionic, or a combination thereof), an emulsifier, a solubilizer, an absorption enhancer, or a combination thereof. In some instances, a single material will meet two or more of the foregoing general classifications.

Exemplary emulsifier/solubilizer include polyoxyethylene castor oil derivatives including polyoxyl 5 castor oil, polyoxyl 9 castor oil, polyoxyl 15 castor oil, polyoxyl 35 castor oil (CREMOPHOR EL from BASF), polyoxyl 40 castor oil, polyoxyl 40 hydrogenated castor oil, polyoxyl 60 hydrogenated castor oil, and the like, or a combination thereof. These emulsifiers/solubilizers are suitable to prepare the formulation as an emulsion or by complexation.

Exemplary non-anionic surfactants include glyceryl monooleate, a polyoxyethylene alkyl ether, a polyoxyethylene castor oil derivative, a polyoxyethylene sorbitan fatty acid ester, a polyoxyethylene stearate, a polysorbate 80 (TWEEN 80), a sorbitan ester, and the like, or a combination thereof. These surfactants are suitable to prepare the formulation as an emulsion or by complexation.

Exemplary anionic surfactants include docusate salts such as sodium, potassium, or calcium docusate; sodium lauryl sulfate, self-emulsifying glyceryl monooleate, and the like, or a combination thereof. These surfactants are suitable to prepare the formulation by complexation.

Absorption enhancers are compounds use to enhance the absorption of the active agent across the nasal membrane either by solubilizing or stabilizing the active agent, altering the property of the nasal membrane, or a combination thereof. Exemplary absorption enhancers include a surfactant (e.g., polidocanol), a bile salt, a fatty acid (e.g., taurodihydrofusidate), chitosan, a cyclodextrin, poly-L-arginine, aminated gelatin, or a combination thereof.

The total amount of surfactant, emulsifier, solubilizer, an absorption enhancer, or a combination thereof in the liquid mucoadhesive intranasal dosage formulation can be from about 0.1 to about 8.0% w/v, specifically about 0.15 to about 6% w/v, and more specifically about 1.0 to about 5.0% w/v.

A pH adjusting agent may optionally be used to render the final liquid mucoadhesive intranasal dosage formulation to a targeted pH. Suitable pH adjusting agents include pharmaceutically acceptable acids, bases, and their salts. Exemplary pH adjusting agents include alkali metal hydroxides (e.g., sodium hydroxide and potassium hydroxide), hydrochloric acid, alkali metal carbonates (e.g., sodium carbonate and potassium carbonate), carbonic acid, or a combination thereof. The pH adjusting agents can be used as solutions or suspensions in a pharmaceutically acceptable solvent. Suitable pharmaceutically acceptable solvents for use with the pH adjusting agent can include purified water, lower alkyl alcohols such as ethanol, a glycol, and the like, or a combination thereof.

The amount of pH adjusting agent can be any amount to result in a desired pH of the final liquid mucoadhesive intranasal dosage formulation. Such amounts can be determined by one having ordinary skill in the art without undue experimentation.

The liquid mucoadhesive intranasal dosage formulation may optionally further comprise an intranasal formulation excipient such as a solid-grade polyethylene glycol (i.e. those that have a molecular weight at or above 1000 such as PEG 1000, PEG 1450, PEG 3350, and the like).

The liquid mucoadhesive intranasal dosage formulation can be administered as an aerosol or spray using a suitable device. The formulations can be administered using a device such as a dropper, atomizer, or spray device. The device can be a squeeze spray device or a metered valve and pump device. An exemplary metered dose device includes 3M™ Nasal MDI.

Also included herein are pharmaceutical kits comprising the liquid mucoadhesive intranasal dosage formulation and a device to intranasally deliver the liquid mucoadhesive intranasal dosage formulation. The kits may further comprise one or more conventional pharmaceutical kit components, such as, for example, one or more containers to aid in facilitating compliance with a particular dosage regimen; one or more carriers; printed instructions, either as inserts or as labels, indicating quantities of the components to be administered, or guidelines for administration. Exemplary kits can be in the form of prepackaged, single use devices, or devices comprising multiple doses. The formulations can be packaged in a dropper, atomizer, or spray device. The device can be a squeeze spray device or a metered valve and pump device. In one embodiment, the kit comprises the liquid mucoadhesive intranasal dosage formulation and a metered dose spray device which can consistently deliver about 50 to about 200 microliters of the formulation per spray to prevent dripping of the formulation to the throat and to promote absorption through the nasal mucosa.

Each dose can contain an amount of about 4 to about 200 mg of methylnaltrexone, a pharmaceutically acceptable salt of methylnaltrexone, a pharmaceutically acceptable ester of methylnaltrexone, or a combination thereof, specifically about 5 to about 150 mg per dose, and yet more specifically 8 to about 100 mg per dose.

The liquid mucoadhesive intranasal dosage formulation can be administered to a patient in need of treatment of opioid-induced side effects, including opioid induced constipation; or administered to a patient in need of treatment of irritable bowel syndrome (IBS).

The features and advantages are more fully shown by the following examples which are provided for purposes of illustration, and are not to be construed as limiting the invention in any way.

EXAMPLES

Example 1. Methylnaltrexone Nasal Solution

A methylnaltrexone bromide nasal solution is prepared using a cellulose-based mucoadhesive. The formulation is provided in Table 1 with amounts in percent weight/volume (% w/v).

TABLE 1

| Ingredients | Lower | Target % w/v | Upper |
|---|---|---|---|
| MNTX-Br (Methylnaltrexone Br) | 0.05 | 0.1 | 2 |
| Microcrystalline cellulose and Carboxymethylcellulose sodium (Avicel ® RC 591, FMC Corporation) | 2.5 | 3 | 3.5 |
| Monobasic sodium phosphate | 0.1 | 0.5525 | 1 |
| Dibasic sodium phosphate | 0.01 | 0.0975 | 0.3 |
| Povidone K29-32 | 1 | 3 | 5 |
| Polyethylene Glycol 1450 | 2 | 5 | 10 |
| Benzalkonium Chloride solution 17% | 0.01 | 0.11449 | 0.5 |
| Benzyl Alcohol | 0.1 | 0.25 | 0.5 |
| EDTA | 0.01 | 0.03 | 0.05 |

TABLE 1-continued

| Ingredients | Lower | Target % w/v | Upper |
|---|---|---|---|
| Sucralose | 0.1 | 0.2 | 0.5 |
| Peppermint Flavor | 0.1 | 0.15 | 1 |
| Water, purified | qs | qs | qs |

The nasal solution formulation is prepared by placing approximately 50% of the batch quantity of purified water in a beaker. Avicel is added to the water in the beaker and mixed to ensure wetting of all powder. In a separate beaker, purified water in an amount of approximately 25% of the batch quantity is added, followed by EDTA, sodium phosphate monobasic, sodium phosphate dibasic, and povidone. To this mixture polyethylene glycol 1450 is added and mixed together. The Avicel solution is added to the povidone solution via an in-line disperser. In a third beaker containing a small quantity of purified water is added the benzalkonium chloride solution, benzyl alcohol, peppermint, Sucralose and methylnaltrexone bromide; the contents are mixed until dissolved. The methylnaltrexone solution is added to the Avicel/povidone solution and mixed well to form a nasal solution. The nasal solution formulation is then packaged in a metered dose spray bottle.

Example 2. Methylnaltrexone Nasal Emulsion

A methylnaltrexone bromide nasal emulsion formulation is prepared using a cellulose-based mucoadhesive and a non-ionic surfactant/emulsifier/solubilizer. The formulation is provided in Table 2.

TABLE 2

| Ingredients | Lower | Target % w/v | Upper |
|---|---|---|---|
| MNTX-Br (Methylnaltrexone Br) | 0.05 | 0.1 | 2 |
| Polysorbate 80 (Tween 80) | 0.05 | 0.1 | 1 |
| Polyethoxylated castor oil (Cremophore EL, BASF) | 0.05 | 0.1 | 1 |
| Microcrystalline cellulose and Carboxymethylcellulose sodium (Avicel ® RC 591, FMC Corporation) | 2.5 | 3 | 3.5 |
| Monobasic sodium phosphate | 0.1 | 0.5525 | 1 |
| Dibasic sodium phosphate | 0.01 | 0.0975 | 0.3 |
| Povidone K29-32 | 1 | 3 | 5 |
| Polyethylene Glycol 1450 | 2 | 5 | 10 |
| Benzalkonium Chloride solution 17% | 0.01 | 0.11449 | 0.5 |
| Benzyl Alcohol | 0.1 | 0.25 | 0.5 |
| EDTA | 0.01 | 0.03 | 0.05 |
| Sucralose | 0.1 | 0.2 | 0.5 |
| Peppermint Flavor | 0.1 | 0.15 | 1 |
| Water, purified | qs | qs | qs |

The nasal emulsion formulation is prepared by placing approximately 50% of the batch quantity of purified water in a beaker. Avicel is added to the water in the beaker and mixed to ensure wetting of all powder. In a separate beaker, purified water in an amount of approximately 25% of the batch quantity is added, followed by Tween 80, Cremophore EL, EDTA, sodium phosphate monobasic, sodium phosphate dibasic, and povidone. To this mixture polyethylene glycol 1450 is added and mixed together. The Avicel solution is added to the povidone solution via an in-line disperser. In a third beaker containing a small quantity of purified water is added the benzalkonium chloride solution, benzyl alcohol, peppermint, Sucralose and methylnaltrexone bromide; the contents are mixed until dissolved. The methylnaltrexone solution is added to the Avicel/povidone solution and mixed well to form a nasal emulsion formulation. The nasal emulsion formulation is then packaged in a metered dose spray bottle.

Example 3. Methylnaltrexone Nasal Formulation: Complexation

A methylnaltrexone bromide nasal formulation is prepared using a cellulose-based mucoadhesive and complexation with an anionic surfactant. The formulation is provided in Table 3.

TABLE 3

| Ingredients | Lower | Target % w/v | Upper |
|---|---|---|---|
| MNTX-Br (Methylnaltrexone Br) | 0.05 | 0.1 | 2 |
| Docusate Sodium | 0.05 | 0.1 | 1 |
| Polyethoxylated castor oil (Cremophore EL, BASF) | 0.05 | 0.1 | 1 |
| Microcrystalline cellulose and Carboxymethylcellulose sodium (Avicel ® RC 591, FMC Corporation) | 2.5 | 3 | 3.5 |
| Monobasic sodium phosphate | 0.1 | 0.5525 | 1 |
| Dibasic sodium phosphate | 0.01 | 0.0975 | 0.3 |
| Povidone K29-32 | 1 | 3 | 5 |
| Polyethylene Glycol 1450 | 2 | 5 | 10 |
| Benzalkonium Chloride solution 17% | 0.01 | 0.11449 | 0.5 |
| Benzyl Alcohol | 0.1 | 0.25 | 0.5 |
| EDTA | 0.01 | 0.03 | 0.05 |
| Sucralose | 0.1 | 0.2 | 0.5 |
| Peppermint Flavor | 0.1 | 0.15 | 1 |
| Water, purified | qs | qs | qs |

The nasal emulsion formulation is prepared by placing approximately 50% of the batch quantity of purified water in a beaker. Avicel is added to the water in the beaker and mixed to ensure wetting of all powder. In a separate beaker, purified water in an amount of approximately 25% of the batch quantity is added, followed by Docusate Sodium, Cremophore EL, EDTA, sodium phosphate monobasic, sodium phosphate dibasic, and povidone. To this mixture polyethylene glycol 1450 is added and mixed together. The Avicel solution is added to the povidone solution via an in-line disperser. In a third beaker containing a small quantity of purified water is added the benzalkonium chloride solution, benzyl alcohol, peppermint, Sucralose and methylnaltrexone bromide; the contents are mixed until dissolved. The methylnaltrexone solution is added to the Avicel/povidone solution and mixed well to form a nasal formulation. The nasal formulation is then packaged in a metered dose spray bottle.

The terms "comprising", "having", "including", and "containing" are to be construed as open-ended terms (i.e., meaning "including, but not limited to"). The terms "a" and "an" do not denote a limitation of quantity, but rather denote the presence of at least one of the referenced item. The term "or" means "and/or". The endpoints of all ranges directed to the same component or property are inclusive and independently combinable. The modifier "about" used in connection with a quantity is inclusive of the stated value and has the meaning dictated by the context (e.g., includes the degree of error associated with measurement of the particular quantity). The term "or a combination thereof" means a combination of one, two, or more of the listed items. Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

Unless defined otherwise, technical and scientific terms used herein have the same meaning as is commonly understood by one of skill in the art to which this invention belongs.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A liquid mucoadhesive intranasal dosage formulation, comprising:
    methylnaltrexone, a pharmaceutically acceptable salt of methylnaltrexone, a pharmaceutically acceptable ester of methylnaltrexone, or a combination thereof;
    a mucoadhesive agent; and
    a liquid carrier;
    wherein the formulation does not substantially drip from the intranasal cavity after administration of a single dose; and
    the methylnaltrexone, a pharmaceutically acceptable salt of methylnaltrexone, a pharmaceutically acceptable ester of methylnaltrexone, or a combination thereof is dissolved in the liquid carrier.

2. The liquid mucoadhesive intranasal dosage formulation of claim 1, comprising about 4 to about 200 mg of methylnaltrexone, a pharmaceutically acceptable salt of methylnaltrexone, a pharmaceutically acceptable ester of methylnaltrexone, or a combination thereof per dose.

3. The liquid mucoadhesive intranasal dosage formulation of claim 1, comprising about 5 to about 150 mg of methylnaltrexone, a pharmaceutically acceptable salt of methylnaltrexone, a pharmaceutically acceptable ester of methylnaltrexone, or a combination thereof per dose.

4. The liquid mucoadhesive intranasal dosage formulation of claim 1, comprising about 8 to about 100 mg of methylnaltrexone, a pharmaceutically acceptable salt of methylnaltrexone, a pharmaceutically acceptable ester of methylnaltrexone, or a combination thereof per dose.

5. The liquid mucoadhesive intranasal dosage formulation of claim 1, comprising methylnaltrexone bromide.

6. The liquid mucoadhesive intranasal dosage formulation of claim 1, wherein the mucoadhesive is an alginate, a cellulose or cellulose derivative, chitosan, a gelling protein, a hydroxyethyl methacrylate, a modified starch, a natural gum, a polysaccharide, a polyacrylic acid, a poly(acrylic acid/divinyl benzene), a poly(lactic acid), a polycarbophil, polyvinyl pyrrolidone, psyllium, a resin, or a combination thereof.

7. The liquid mucoadhesive intranasal dosage formulation of claim 1, wherein the mucoadhesive is microcrystalline cellulose, carboxymethylcellulose sodium, polyvinyl pyrrolidone, or a combination thereof.

8. The liquid mucoadhesive intranasal dosage formulation of claim 1, wherein the mucoadhesive agent is present in an amount of about 1.0 to about 25% w/v.

9. The liquid mucoadhesive intranasal dosage formulation of claim 1, wherein the liquid carrier is purified water, a pharmaceutically acceptable organic liquid carrier, or a combination thereof.

10. The liquid mucoadhesive intranasal dosage formulation of claim 1, further comprising an intranasal formulation excipient, a buffering agent, a flavoring agent, a sweetening agent, a tonicity agent, an antimicrobial preservative, an antimicrobial preservative synergist, a surfactant, an emulsifier, a solubilizer, an absorption enhancer, or a combination thereof.

11. The liquid mucoadhesive intranasal dosage formulation of claim 10, wherein the buffering agent is a sodium phosphate.

12. The liquid mucoadhesive intranasal dosage formulation of claim 10, wherein the antimicrobial preservative is benzalkonium chloride, benzyl alcohol, sodium benzoate or a combination thereof; and
wherein the antimicrobial preservative synergist is ethylenediaminetetraacetic acid or a pharmaceutically acceptable salt thereof.

13. The liquid mucoadhesive intranasal dosage formulation of claim 10, wherein the sweetening agent is an artificial sweetener.

14. The liquid mucoadhesive intranasal dosage formulation of claim 10, wherein the surfactant is a non-ionic surfactant.

15. The liquid mucoadhesive intranasal dosage formulation of claim 10, wherein the surfactant, emulsifier, solubilizer, an absorption enhancer, or a combination thereof is a polyoxyethylene castor oil derivative, a glyceryl monooleate, a polyoxyethylene alkyl ether, a polyoxyethylene sorbitan fatty acid ester, a polyoxyethylene stearate, a polysorbate 80, a sorbitan ester, a docusate salt, sodium lauryl sulfate, a self-emulsifying glyceryl monooleate, or a combination thereof.

16. The liquid mucoadhesive intranasal dosage formulation of claim 1, in the form of a solution, emulsion, or complexation formulation.

17. The liquid mucoadhesive intranasal dosage formulation of claim 1, wherein the formulation can be administered as an aerosol or spray.

18. A kit comprising, the liquid mucoadhesive intranasal dosage formulation of claim 1, packaged in a dropper, atomizer, or spray device.

19. The kit of claim 18, wherein the kit comprises a metered dose spray device which can deliver about 50 to about 200 microliters of formulation per spray.

20. A method of administering methylnaltrexone to a patient in need thereof, comprising
intranasally administering to a patient a liquid mucoadhesive intranasal dosage formulation comprising
methylnaltrexone, a pharmaceutically acceptable salt of methylnaltrexone, a pharmaceutically acceptable ester of methylnaltrexone, or a combination thereof;
a mucoadhesive; and
a liquid carrier,
wherein the formulation does not substantially drip from the intranasal cavity after administration of a single dose; and
the methylnaltrexone, a pharmaceutically acceptable salt of methylnaltrexone, a pharmaceutically acceptable ester of methylnaltrexone, or a combination thereof is dissolved in the liquid carrier.

21. The method of claim 20 to treat a patient suffering from opioid-induced constipation or irritable bowel syndrome.

22. The method of claim 20, wherein the formulation is administered in an amount of about 50 to about 200 microliters to prevent dripping to the throat and promote absorption through the nasal mucosa.

23. A liquid mucoadhesive intranasal dosage formulation, comprising:
about 0.05 to about 2% w/v methylnaltrexone bromide;
about 1.0 to about 25% w/v of a mucoadhesive agent, wherein the mucoadhesive is microcrystalline cellulose, carboxymethylcellulose sodium, polyvinyl pyrrolidone, or a combination thereof; and
a liquid carrier comprising purified water;
wherein the formulation does not substantially drip from the intranasal cavity after administration of a single dose; and
the methylnaltrexone bromide is dissolved in the liquid carrier.

24. A kit comprising, the liquid mucoadhesive intranasal dosage formulation of claim 23, packaged in a metered dose spray device which can deliver about 50 to about 200 microliters of formulation per spray.

* * * * *